US010807961B2

(12) United States Patent
Koike et al.

(10) Patent No.: US 10,807,961 B2
(45) Date of Patent: Oct. 20, 2020

(54) METHOD FOR PRODUCING PROPYLENE OXIDE

(71) Applicant: Sumitomo Chemical Company, Limited, Tokyo (JP)

(72) Inventors: Hirofumi Koike, Ichihara (JP); Tomonori Kawabata, Ichihara (JP); Takuo Takemoto, Rabigh (SA); Motoshi Nakamura, Ichihara (JP); Satoru Takemoto, Ichihara (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/320,329

(22) PCT Filed: Jul. 25, 2017

(86) PCT No.: PCT/JP2017/026783
§ 371 (c)(1),
(2) Date: Jan. 24, 2019

(87) PCT Pub. No.: WO2018/021271
PCT Pub. Date: Feb. 1, 2018

(65) Prior Publication Data
US 2020/0140403 A1    May 7, 2020

(30) Foreign Application Priority Data
Jul. 29, 2016 (JP) .................. 2016-150489

(51) Int. Cl.
*C07D 303/04* (2006.01)
*B01J 21/08* (2006.01)
(Continued)

(52) U.S. Cl.
CPC ............ *C07D 303/04* (2013.01); *B01J 21/08* (2013.01); *C07D 301/19* (2013.01); *C07D 301/32* (2013.01); *C07D 301/08* (2013.01)

(58) Field of Classification Search
CPC .. C07D 303/04; C07D 301/08; C07D 301/19; C07D 301/32; B01J 21/08
(Continued)

(56) References Cited

U.S. PATENT DOCUMENTS

| 8,466,302 | B1  | 6/2013  | Chuang et al. |
| 2004/0254386 | A1* | 12/2004 | Tsuji ................... C07D 301/19 549/529 |

(Continued)

FOREIGN PATENT DOCUMENTS

| EP | 2612849 A1  | 7/2013 |
| JP | 2003-261482 A | 9/2003 |

(Continued)

OTHER PUBLICATIONS

Extended European Search Report dated Dec. 16, 2019 in EP Application No. 17834277.0.

(Continued)

*Primary Examiner* — Taylor V Oh
(74) *Attorney, Agent, or Firm* — Panitch Schwarze Belisario & Nadel LLP (57) ABSTRACT

A method for producing propylene oxide involves an oxidation step, a distillation step, an epoxidation step, and a separation step. The distillation step involves distilling the reaction mixture containing cumene hydroperoxide to separate it into a concentrate containing cumene hydroperoxide and a distillate. The reaction mixture is continuously distilled so that the ratio of the flow rate of the distillate to the flow rate of the reaction mixture to be distilled is 0.037 to 0.13. The epoxidation step involves obtaining a reaction mixture containing propylene oxide and cumyl alcohol by contacting the concentrate with propylene in the presence of a catalyst in one or more reactors to cause a reaction between propylene and cumene hydroperoxide in the concentrate, in (Continued)

which the outlet temperature of the final reactor is adjusted to 115° C. or more and less than 140° C.

2 Claims, 1 Drawing Sheet

(51) Int. Cl.
 *C07D 301/19* (2006.01)
 *C07D 301/32* (2006.01)
 *C07D 301/08* (2006.01)
(58) Field of Classification Search
 USPC .......................................................... 549/531
 See application file for complete search history.

(56) References Cited

U.S. PATENT DOCUMENTS

| | | | |
|---|---|---|---|
| 2007/0043226 A1* | 2/2007 | Muller | C07D 301/12 549/529 |
| 2008/0035468 A1 | 2/2008 | Nakayama et al. | |
| 2010/0048925 A1 | 2/2010 | Yamamoto et al. | |
| 2010/0094029 A1 | 4/2010 | Chiwaki et al. | |

FOREIGN PATENT DOCUMENTS

| | | |
|---|---|---|
| JP | 2003-261552 A | 9/2003 |
| JP | 2003-327576 A | 11/2003 |
| JP | 2006-008544 A | 1/2006 |
| JP | 2006-124332 A | 5/2006 |
| JP | 2007-063256 A | 3/2007 |
| JP | 2008-142584 A | 6/2008 |
| JP | 2008-266304 A | 11/2008 |
| JP | 2009-215228 A | 9/2009 |
| JP | 2009-215229 A | 9/2009 |
| JP | 2014-009183 A | 1/2014 |
| WO | 2005030743 A1 | 4/2005 |
| WO | 2008123384 A1 | 10/2008 |

OTHER PUBLICATIONS

Int'l Preliminary Report on Patentability dated Feb. 7, 2019 in Int'l Application No. PCT/JP2017/026783.
Int'l Search Report dated Oct. 24, 2017 in Int'l Application No. PCT/JP2017/026783.
Office Action dated Jul. 17, 2020 in IN Application No. 201947006652.

* cited by examiner

METHOD FOR PRODUCING PROPYLENE OXIDE

CROSS-REFERENCE TO RELATED APPLICATION

This application is a Section 371 of International Application No. PCT/JP2017/026783, filed Jul. 25, 2017, which was published in the Japanese language on Feb. 1, 2018 under International Publication No. WO 2018/021271 A1, and claims priority under 35 U.S.C. § 119(b) to Japanese Application No. 2016-150489, filed Jul. 29, 2016, the disclosures of which are incorporated herein by reference in their entirety.

TECHNICAL FIELD

The present invention relates to a method for producing propylene oxide.

BACKGROUND ART

As a method for producing propylene oxide, a method of causing a reaction between an organic peroxide and propylene in the presence of a catalyst is known. In the reaction mixture obtained by the reaction, oxygen-containing compounds such as water, hydrocarbon, methanol, formaldehyde, propionaldehyde, acetone and methyl formate are typically contained as impurities other than propylene oxide. Methyl formate in propylene oxide degrades the quality of propylene oxide for use as a raw material of various chemical products.

As a method for reducing methyl formate in propylene oxide, Patent Literature 1 describes a method which applies extractive distillation with an extractive distillation column to propylene oxide containing methyl formate as an impurity by using an extracting agent of hydrocarbons having 7 to 10 carbon atoms, adds water to a distillate liquid from the column top of the extractive distillation column so as to be separated into an oil layer and an aqueous layer, recycles the oil layer into the extractive distillation column while removing the aqueous layer outside the system, and then obtains propylene oxide with a reduced concentration of methyl formate as a column bottom liquid in the extractive distillation column.

As another method for reducing methyl formate in propylene oxide, Patent Literature 2 describes a method of washing propylene oxide containing methyl formate with water to remove methyl formate in propylene oxide, wherein the pH of an aqueous layer washed with water is adjusted to 7 to 9, and then the aqueous layer is contacted with an extracting agent.

CITATION LIST

Patent Literature

Patent Literature 1: Japanese Unexamined Patent Publication No. 2006-8544.
Patent Literature 2: Japanese Unexamined Patent Publication No. 2006-124332.

SUMMARY OF INVENTION

Technical Problem

Having a boiling point close to that of propylene oxide, methyl formate is one of the most difficult impurities to be separated from propylene, so that further improvement in direction of reducing methyl formate from propylene oxide containing methyl formate is not easy.

Further, according to the conventional method, in the case where the methyl formate concentration of propylene oxide to be purified is high, the energy required for purification increases.

The purpose of the present invention is to reduce the methyl formate concentration of a reaction mixture obtained in an epoxidation step of the method for producing propylene oxide so that the load for removing methyl formate in a separation step of propylene oxide (e.g., thermal energy required for the removal) is decreased.

Solution to Problem

Under the circumstances, the present inventors found that in producing propylene oxide through an oxidation step, a distillation step, an epoxidation step and a propylene oxide separation step so as to cause a reaction between cumene hydroperoxide and propylene, controlling of the distillation conditions in the distillation step of a reaction mixture containing cumene hydroperoxide obtained in the oxidation step and the outlet temperature of the final reactor in the epoxidation step performed using one or more reactors enables the methyl formate concentration of the reaction mixture containing propylene oxide and cumyl alcohol obtained in the epoxidation step to be controlled, so that the present invention was achieved.

In other words, the present invention provides either one of the following methods.

[1] A method for producing propylene oxide comprising the following steps (1) to (4):

(1) Oxidation step: a step of obtaining a reaction mixture containing cumene hydroperoxide by contacting cumene with an oxygen-containing gas to cause a reaction between cumene and oxygen in the gas;

(2) Distillation step: a step of distilling the reaction mixture containing cumene hydroperoxide obtained in the oxidation step to be separated into a concentrate containing cumene hydroperoxide and a distillate, wherein the reaction mixture is continuously distilled under a condition where a ratio of a flow rate of the distillate (D) to a flow rate of the reaction mixture to be distilled (F), D/F, is 0.037 or more and 0.13 or less, provided that the flow rate of the reaction mixture is a weight of the reaction mixture distilled per unit time, whereas the flow rate of the distillate is a weight of the distillate distilled off per unit time;

(3) Epoxidation step: a step of obtaining a reaction mixture containing propylene oxide and cumyl alcohol by contacting the concentrate containing cumene hydroperoxide obtained in the distillation step with propylene in the presence of a catalyst in one or more reactors to cause a reaction between propylene and cumene hydroperoxide in the concentrate, wherein an outlet temperature of the final reactor of the one or more reactors is adjusted to 115° C. or more and less than 140° C.; and (4) Separation step: a step of separating crude propylene oxide by distilling the reaction mixture containing propylene oxide and cumyl alcohol obtained in the epoxidation step.

[2] The method for producing propylene oxide according to item [1], wherein the reaction mixture containing propylene oxide and cumyl alcohol in the epoxidation step contains methyl formate, and a concentration of methyl formate in the reaction mixture is 10 ppm by weight or more and less than 30 ppm by weight based on the weight of propylene oxide in the reaction mixture.

[3] The method for producing propylene oxide according to item [1] or [2], wherein the catalyst in the epoxidation step comprises a titanium-containing silicon oxide.

Advantageous Effects of Invention

According to the present invention, in producing propylene oxide, the methyl formate concentration of the reaction mixture containing propylene oxide and cumyl alcohol obtained in the epoxidation step can be reduced to decrease the load for removing methyl formate in a propylene oxide purification step.

DESCRIPTION OF EMBODIMENTS

[Method for Producing Propylene Oxide]

A method for producing propylene oxide of the present invention comprises: (1) an oxidation step, (2) a distillation step, (3) an epoxidation step, and (4) a separation step described in detail as follows.

(1) Oxidation Step

The oxidation step is a step of obtaining a reaction mixture containing cumene hydroperoxide by contacting cumene with an oxygen-containing gas to cause a reaction between cumene and oxygen in the gas.

Cumene in a mixture state containing cumene and impurities may be supplied to the oxidation step. The cumene content of the mixture containing cumene and impurities is preferably 90 wt % or more per 100 wt % of the mixture.

Examples of the oxygen-containing gas include oxygen, air and air with condensed oxygen.

The cumene hydroperoxide content of the reaction mixture containing cumene hydroperoxide is preferably 5 to 80 wt %, more preferably 5 to 60 wt %, still more preferably 5 to 40 wt %, per 100 wt % of the reaction mixture.

Cumene is oxidized by oxygen to produce cumene hydroperoxide. The oxidation of cumene is an autoxidation caused by an oxygen-containing gas such as air and air with condensed oxygen. The oxidation may be performed in the presence of an alkaline aqueous solution. The alkaline aqueous solution may be any aqueous solution with alkaline nature, and a fresh alkaline solution, an aqueous solution recovered from the oxidation step, an aqueous solution prepared by mixing an aqueous solution recovered from the oxidation step with a fresh alkaline solution, or the like is used. Examples of the fresh alkaline aqueous solution for normal use include an aqueous solution prepared by dissolving alkaline metal compounds in water such as NaOH and KOH, alkaline earth metal compounds such as $Mg(OH)_2$ and $Ca(OH)_2$, alkaline metal carbonates such as $Na_2CO_3$ and $NaHCO_3$, or ammonia and $(NH_4)_2CO_3$ or alkaline metal ammonium carbonates.

The recovery of the aqueous solution in the oxidation step can be performed by separating a liquid phase produced in the oxidation step into an oil phase and an aqueous phase and recovering the aqueous phase. The oxidation reaction temperature is usually 50 to 200° C., preferably 60 to 180° C., more preferably 70 to 150° C. The reaction pressure is usually between atmospheric pressure and 5000 kPaG, preferably 10 to 2000 kPaG, more preferably 20 to 1000 kPaG.

Cumene, cumyl alcohol, acetophenone, ethylbenzene, organic acids such as phenol, formic acid, acetic acid, propionic acid, benzoic acid, oxalic acid, malonic acid and lactic acid, and water are contained in the reaction mixture containing cumene hydroperoxide, as components thereof other than cumene hydroperoxide.

It is preferable that the reaction mixture containing cumene hydroperoxide be distilled in the following distillation step after removal of the aqueous phase by performing oil/water separation. It is also preferable that the oil phase after removal of aqueous phase be washed with an aqueous solution of an alkaline compound from the viewpoint of removing the organic acids.

Examples of the aqueous solution of the alkaline compound for normal use include an aqueous solution prepared by dissolving in water alkaline metal compounds such as NaOH and KOH, alkaline earth metal compounds such as $Mg(OH)_2$ and $Ca(OH)$, alkaline metal carbonates such as $Na_2CO_3$ and $NaHCO_3$, or ammonia and $(NH_4)CO_3$ or alkaline metal ammonium carbonates. It is preferable that the alkaline compound used be removed before distillation in the following distillation step, usually by washing with added water. The concentration of alkaline compound in the reaction mixture containing cumene hydroperoxide to be supplied to the following distillation step is preferably 1000 ppm by weight or less, more preferably 500 ppm by weight or less, in terms of alkaline metal per 100 wt % of the reaction mixture containing cumene hydroperoxide.

(2) Distillation Step

The distillation step is a step of distilling the reaction mixture containing cumene hydroperoxide obtained in the oxidation step so as to be separated into a concentrate containing cumene hydroperoxide and a distillate, wherein the reaction mixture is continuously distilled under a condition where the ratio of the flow rate of the distillate (D) to the flow rate of the reaction mixture to be distilled (F), D/F, is 0.037 or more and 0.13 or less. Note that the flow rate of the reaction mixture (F) is the weight of the reaction mixture distilled per unit time, whereas the flow rate of the distillate (D) is the weight of the distillate distilled off per unit time. The length of unit time and the unit of weight are the same between the flow rate (F) and the flow rate (D).

The distillation is performed in order to distill mainly water from the reaction mixture containing cumene hydroperoxide obtained in the oxidation step, and a concentrate having a higher concentration of cumene hydroperoxide than that of the reaction mixture can be obtained.

The distillation is performed at a distillation column. The distillation column may be in either form of a packed column or a plate column. In the distillation, the reaction mixture containing cumene hydroperoxide is continuously supplied to a distillation column so as to be separated into a concentrate containing cumene hydroperoxide and a distillate.

It is preferable that the distillation be performed through adjustment of the temperature and pressure at the bottom of the distillation column to a temperature and a pressure such that cumene hydroperoxide is not be evaporated and water is evaporated. The reaction mixture containing cumene hydroperoxide is heated by adding heat energy to the bottom of a distillation column, so that water and the like contained in the reaction mixture are evaporated as gas to rise to the upper part of the distillation column. The gas rising to the upper part of the distillation column is cooled at the upper part so as to continuously discharge a distillate in a liquid state mainly composed of cumene and water from a distillation part in the vicinity of the distillation column top. On the other hand, from the lower part of the distillation column, a concentrate is continuously discharged. The concentrate is transported to an implementation location of the epoxidation step. The sum of the flow rate of the distillate to be discharged (D) and the flow rate of the concentrate is approximately equal to the flow rate of the reaction mixture to be supplied (F). By changing the amount of thermal energy added to the bottom of a distillation column, the amount of evaporating water and the like can be adjusted, so that the ratio between the flow rate of the distillate to be discharged (D) and the flow rate of the concentrate can be changed. The ratio between the flow rate of the distillate (D) and the flow rate of the concentrate can be adjusted independently from the flow of the reaction mixture to be distilled (F).

By adjusting the flow rate of the distillate (D) thus adjusted and the flow rate of the reaction mixture to be distilled (F) respectively, D/F can be adjusted.

Hereupon, the flow rate (F) is a flow meter reading or a measured value at the inlet part of a distillation column, and the flow rate (D) is a flow meter reading or a measured value at the distillation part of a distillation column. The flow rate (F) can be controlled by a method for changing the amount of the reaction mixture containing cumene hydroperoxide supplied, and the flow rate (D) can be controlled by a method for changing the amount of thermal energy added to the bottom of a distillation column.

The concentration of cumene hydroperoxide in the concentrate containing cumene hydroperoxide is higher than the concentration of cumene hydroperoxide in the reaction mixture containing cumene hydroperoxide to be distilled, being, for example, 10 wt % to 90 wt % per 100 wt % of the concentrate containing cumene hydroperoxide.

In order to reduce the methyl formate concentration of the reaction mixture containing propylene oxide and cumyl alcohol obtained in the following epoxidation step, D/F is preferably 0.040 or more, more preferably 0.045 or more. D/F is preferably 0.12 or less, more preferably 0.11 or less, such that the amount of energy required for distillation in the distillation step does not excessively increase.

In the distillation step, the column top temperature of the distillation column is usually in the range of 30 to 150° C. and the column top pressure is usually in the range of −100 to 100 kPaG, G whereas the column bottom temperature is usually in the range of 30 to 150° C. and the column bottom pressure us usually in the range of −100 to 100 kPaG.

The distillate obtained comprises, for example, 90 wt % to 99 wt % cumene per 100 wt % of the distillate. From the distillate, an aqueous phase is removed to make an oil phase by a method such as liquid/liquid separation or the like, so that the oil phase can be recycled to the oxidation step for use as a raw material in the oxidation step.

(3) Epoxidation Step

The epoxidation step is a step of obtaining a reaction mixture containing propylene oxide and cumyl alcohol by contacting the concentrate containing cumene hydroperoxide obtained in the distillation step with propylene in one or more reactors in the presence of a catalyst to cause a reaction between propylene and cumene hydroperoxide in the concentrate, wherein the outlet temperature of the final reactor of the one or more reactors is adjusted to 115° C. or more and less than 140° C.

In the epoxidation step, the epoxidation reaction is performed using, for example, 1 or more and less than 10 reactors. In the case where 2 or more reactors are used, the reactors adjacent to each other are usually connected through a connection part such as a pipe. In order to control the temperature of the reaction mixture supplied to each of the reactors, equipment such as a heat exchanger and a thermoregulator may be installed between the two reactors.

In the epoxidation step, it is preferable that the number of the reactors in the epoxidation step be 2 or more from the viewpoint of suppressing excessive increase in the temperature of the reaction mixture to perform the epoxidation reaction in a stable state.

Each of the reactors in which the epoxidation reaction is performed is filled with a catalyst for use in the epoxidation reaction. In the present specification, a reactor filled with at least 10 wt %, preferably 20 wt %, of a catalyst based on the whole amount of the catalyst used in the epoxidation step is the reactor in which the epoxidation reaction is performed. The first reactor is a reactor in which the concentrate containing cumene hydroperoxide obtained in the distillation step comes into contact with the catalyst for the first time. The final reactor among one or more reactors is a final reactor in which the epoxidation reaction is performed and a reactor from which a reaction mixture containing propylene oxide and cumyl alcohol is supplied to a separation step described as follows. In the case where 2 or more reactors are used, all of the two or more reactors are connected in series or in parallel in an embodiment.

Figure 1:
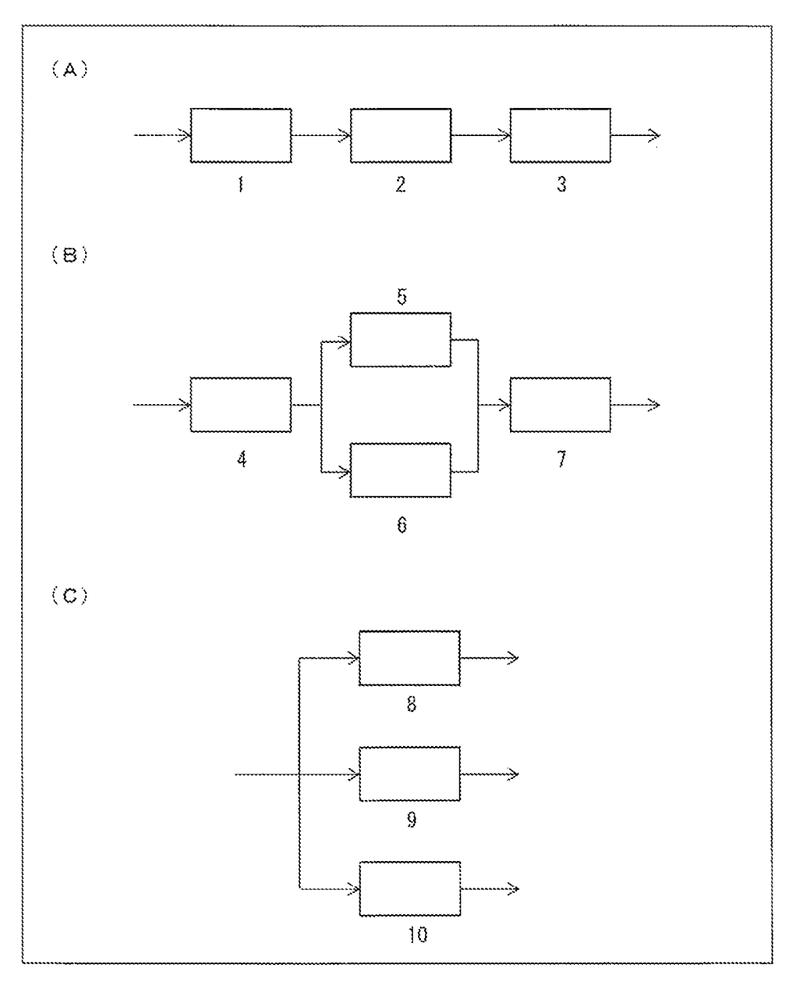
FIG. 1 is a chart showing a configuration of reactors in which an epoxidation reaction is performed in the epoxidation step in an embodiment of the present invention.

An embodiment in which 2 or more reactors are used in the epoxidation step is described with reference to FIG. 1 as follows. In the drawing, the distillation step described in the item (2) is shown in the left side, and a separation step described in the following item (4) is shown in the right side, wherein reactors 1 to 10 are the reactors in which the epoxidation reaction is performed.

In an embodiment shown in (A) in the drawing, the reactors 1 to 3 are connected in series, and the reactor 1 is the first reactor. At the downstream of the reactor 1, the reactor 2 is connected, and at the downstream of the reactor 2, the reactor 3 is connected. A reaction product obtained in the reactor 1 is supplied to the reactor 2, and a reaction product obtained in the reactor 2 is supplied to the reactor 3, respectively. The reactor 3 is the final reactor.

In an embodiment shown in (B) in the drawing, the reactor 4 is the first reactor. At the downstream of the reactor 4, the reactors 5 and 6 are connected in parallel, and a reaction product obtained in the reactor 4 is supplied to the reactors 5 and 6. At the downstream of the reactors 5 and 6, the reactor 7 is connected, and a reaction product obtained in the reactors 5 and 6 is supplied to the reactor 7. The reactor 7 is the final reactor.

In an embodiment shown in (C) in the drawing, the reactors 8 to 10 are connected in parallel, and a concentrate containing cumene hydroperoxide obtained in the distillation step described in the item (2) is supplied to each of the reactors. Any of the reactors 8 to 10 is the first reactor and the final reactor.

In the epoxidation step, in the case where the number of reactors for use is 2 or more, the temperature of the reaction mixture at the inlet of each of the reactors can be arbitrarily adjusted through a heat exchanger or a thermoregulator installed upstream of the inlet of the reactor.

In the epoxidation step, in the case where the number of reactors for use is 2 or more, the temperature of the reaction mixture at the outlet of the first reactor is preferably 90° C. or more, more preferably 100° C. or more. The temperature of the reaction mixture at the outlet of each of the reactors can be adjusted by a method of controlling the temperature of the reaction mixture at the inlet of the reactor with consideration of the heat generation caused by the epoxidation reaction, a method of using a thermoregulator installed in each of the reactors, or the like.

In order to reduce the methyl formate concentration of the reaction mixture containing propylene oxide and cumyl alcohol obtained in the epoxidation step, the outlet temperature of the final reactor is less than 140° C., preferably 139° C. or less, more preferably 138° C. or less. From the viewpoint of improving the epoxidation reaction rate, the outlet temperature of the final reactor is 115° C. or more, preferably 117° C. or more, more preferably 120° C. or more. Herein, the outlet temperature of the final reactor is the temperature of the reaction mixture containing propylene oxide and cumyl alcohol obtained in the epoxidation step after passing through the catalyst packed in the final reactor, which can be measured by reading of a thermometer installed in the vicinity of the outlet of the final reactor.

The temperature of the reaction mixture containing propylene oxide and cumyl alcohol in the vicinity of the outlet of the final reactor is measured without heating or cooling of the reaction mixture by using a heat exchanger or a thermoregulator.

In an embodiment, the outlet temperature of the final reactor is controlled through control of the inlet temperature of the final reactor. In another embodiment, the outlet temperature of the final reactor is controlled through control of the temperature in the final reactor. The difference by subtracting the inlet temperature of the final reactor from the outlet temperature of the final reactor is more preferably 30° C. or less, still more preferably 15° C. or less.

It is preferable that the catalyst used in the epoxidation step be a catalyst comprising a titanium-containing silicon oxide from the viewpoint of obtaining propylene oxide at a high yield. The titanium-containing silicon oxide is a compound containing titanium chemically bonded to a silicon oxide, and examples of the catalyst comprising a titanium-containing silicon oxide include a titanium compound supported on a silica support, a composite of a titanium compound and a silicon oxide produced by a coprecipitation method or a sol-gel method, and a titanium-containing zeolite compound. Herein, the term "zeolite compound" means a compound having a structure recorded in "International Zeolite Association". Examples of the catalyst comprising a preferred titanium-containing silicon oxide include: catalysts described in Japanese Patent No. 3731384, Japanese Patent No. 3797107, and the like; catalysts described in US 2005/014960A1, US 2007/260074A1, and the like; Ti-MCM-41 described in U.S. Pat. No. 5,783,167, and the like; Ti-MCM-48 described in Japanese Unexamined Patent Publication No. H7-300312, and the like; Ti-HMS described in Nature 368 (1994) p. 321, CN101348472B, CN101307039B, CN101279960B, CN102311363B, CN102872847B, CN103030611B, and the like; Ti-SBA-15, TS-1 and TS-2 described in Chemistry of Material 14, 2002, p. 1657, and the like; and Ti-MWW and the precursor thereof described in Chemistry Letters 2000, p. 774, and the like.

The epoxidation reaction is performed by contacting propylene and cumene hydroperoxide with a catalyst. The epoxidation reaction can be performed in a liquid phase, using a solvent, which is required to be a liquid at the temperature and pressure during the epoxidation reaction, and to be substantially inert to the reaction raw materials and products. The solvent may be a material present in the concentrate containing cumene hydroperoxide obtained in the distillation step, and for example, in the case where the concentrate contains cumene, the cumene can be the solvent. Examples of the solvents other than cumene include monocyclic aromatic solvents such as benzene, toluene, chlorobenzene and orthodichlorobenzene, and alkane solvents such as octane, decane and dodecane.

The epoxidation reaction pressure is adjusted such that the reaction mixture can be maintained in a liquid state, and is usually 100 to 10000 kPaG.

The epoxidation reaction can be favorably performed in a fixed bed mode, in the case of a large-scale industrial operation.

The propylene oxide content of the reaction mixture containing propylene oxide and cumyl alcohol obtained in the epoxidation step is preferably 1 to 31 wt %, more preferably 1 to 23 wt %, still more preferably 1 to 16 wt %, per 100 wt % of the reaction mixture. The cumyl alcohol content is preferably 5 to 80 wt %, more preferably 5 to 60 wt %, still more preferably 5 to 40 wt %, per 100 wt % of the reaction mixture.

In the epoxidation step, the molar ratio of propylene to cumene hydroperoxide (propylene/cumene hydroperoxide) is usually 2/1 to 50/1.

Unreacted propylene may be collected after the epoxidation step, such that a step of recycling the collected propylene as a raw material in the epoxidation step to the epoxidation step is further performed.

In the epoxidation step, in the case where the reaction mixture containing propylene oxide and cumyl alcohol contains methyl formate, it is preferable that the methyl formate concentration of the reaction mixture be 10 ppm by weight or more and less than 30 ppm by weight based on the weight of propylene oxide in the reaction mixture. The methyl formate concentration can be directly measured by gas chromatography analysis of the reaction mixture.

Since the boiling points of methyl formate and the boiling point of propylene oxide are close to each other, it can be presumed that almost all of the methyl formate contained in the reaction mixture obtained in the epoxidation step is contained in a mixture containing propylene oxide obtained in a separation step described below. It is therefore presumed that the ratio between propylene oxide and methyl formate contained in the reaction mixture obtained in the epoxidation step and the ratio between propylene oxide and methyl formate contained in the mixture containing propylene oxide obtained in the separation step are approximately the same as each other. In other words, it may be regarded that the methyl formate concentration based on the weight of propylene oxide in the mixture containing propylene oxide obtained in the separation step is approximately the same as the methyl formate concentration based on the weight of propylene oxide in the reaction mixture obtained in the epoxidation step.

(4) Separation Step

The separation step is a step of distilling the reaction mixture containing propylene oxide and cumyl alcohol obtained in the epoxidation step so as to separate crude propylene oxide.

The reaction mixture containing propylene oxide and cumyl alcohol to be distilled in the separation step also contains a reaction mixture obtained through removal of unreacted propylene after the epoxidation step.

The pressure of the distillation is usually 100 to 5000 kPaG, preferably 100 to 3000 kPaG, and the column top temperature is usually −50 to 150° C. Examples of the distillation process include a method using a distillation column, and distillation may be performed using a plurality of distillation columns.

The content of propylene oxide in the separated crude propylene oxide is usually 99 wt %/o or more per 100 wt % of the crude propylene oxide.

The crude propylene oxide separated by distillation usually contains water, hydrocarbons and oxygen-containing compounds as impurities. Examples of the hydrocarbons include hydrocarbons having 3 to 7 carbons. Examples of the oxygen-containing compounds include compounds such as methanol, acetaldehyde, acetone, propionaldehyde and methyl formate.

In order to remove the impurities, known distillation techniques may be appropriately combined to further purify the crude propylene oxide, and it is preferable that purifying be performed through combination of extractive distillation with an extracting agent of hydrocarbons having 6 to 10 carbon atoms and other distillation, from the viewpoint of efficiently removing water, hydrocarbons, and oxygen-containing compounds.

Examples of the extracting agents of hydrocarbons having 6 to 10 carbon atoms include straight-chain saturated hydrocarbons such as n-hexane, n-heptane, n-octane, n-nonane and n-decane, and branched saturated hydrocarbons such as 2-methylpentane, 3-methylpentane, 2,3-dimethylbutane, 2,2-dimethylbutane, 2,2-dimethylpentane, 2,3-dimethylpentane, 2,2-dimethylhexane and 2,3-dimethylhexane. These extracting agents may be used either singly or as a mixture of those compounds.

The types and the operation conditions of the extractive distillation column and the other distillation column, and the amount of the extracting agent used and the like can be appropriately determined depending on the product quality of propylene oxide required.

In the separation step, as a residual product after separation of the crude propylene oxide by distillation, a residual mixture containing cumyl alcohol is obtained. The residual mixture may be supplied to a cumene conversion step and the like described below on an as needed basis.

(5) Other Steps

In an embodiment of the method for producing propylene oxide of the present invention, a cumene conversion step and a cumene recovery step described below may be further provided on if necessary.

(5-1) Cumene Conversion Step

The cumene conversion step is a step of obtaining a reaction mixture containing cumene by converting cumyl alcohol in the residual mixture containing cumyl alcohol obtained in the (4) separation step into cumene.

In an aspect, the cumene conversion step comprises a step of obtaining a mixture containing α-methylstyrene by dehydrating cumyl alcohol in the residual mixture containing cumyl alcohol obtained in the separation step in the presence of a catalyst (hereinafter, referred to as "dehydration step"), and a step of obtaining a reaction mixture containing cumene by contacting the mixture containing α-methylstyrene obtained in the dehydration step with hydrogen in the presence of a catalyst so as to cause a reaction between α-methylstyrene in the mixture and hydrogen (hereinafter, referred to as "hydrogenation step").

In another aspect, the cumene conversion step is a step of obtaining a reaction mixture containing cumene by contacting the residual mixture containing cumyl alcohol obtained in the separation step with hydrogen in the presence of a catalyst so as to cause a reaction between cumyl alcohol in the residual mixture and hydrogen (hereinafter, referred to as "hydrogenolysis step").

The case where a cumene conversion step comprises a dehydration step and a hydrogenation step is described as follows.

Examples of the catalyst for use in the dehydration step (hereinafter, referred to as "dehydration catalyst") include acids such as sulfuric acid, phosphoric acid and p-toluene sulfonic acid, and metal oxides such as activated alumina, titania, zirconia, silica-alumina and zeolite. From the viewpoint of improving the reaction efficiency, a solid catalyst is preferred, and activated alumina is more preferred.

The dehydration reaction in the dehydration step is usually performed by contacting cumyl alcohol with a dehydration catalyst. In an embodiment, since the dehydration reaction is followed by the hydrogenation reaction in the hydrogenation step, cumyl alcohol may be contacted with a dehydration catalyst in the presence of hydrogen. The dehydration reaction may be performed in a liquid phase in the presence of a solvent. The solvent is required to be substantially inert to the reaction raw materials and products. The solvent may be a substance present in the residual mixture containing cumyl alcohol to be used. For example, in the case where the residual mixture containing cumyl alcohol contains cumene, the cumene can be used as the solvent and no other solvent may be used. The dehydration reaction temperature is usually 50 to 450° C., preferably 150 to 300° C. The dehydration pressure is usually 10 to 10000 kPaG, preferably 500 to 4000 kPaG, more preferably 1000 to 2000 kPaG.

Examples of the catalyst used in the hydrogenation step (hereinafter, referred to as "hydrogenation catalyst") include catalysts comprising metals in group 10 or group 11 in the periodic table, specifically including catalysts comprising nickel, catalysts comprising palladium, catalysts comprising platinum and catalyst comprising copper. From the viewpoints of inhibition of the nucleus hydrogenation reaction of an aromatic ring and the high yield, catalysts comprising nickel, catalysts comprising palladium or catalysts comprising copper are preferred. As the catalysts comprising nickel, nickel, nickel-alumina, nickel-silica and nickel-carbon are preferred; as the catalysts comprising palladium, palladium-alumina, palladium-silica and palladium-carbon are preferred; and as the catalysts comprising copper, copper, Raney copper, copper-chromium, copper-zinc, copper-chromium-zinc, copper-silica and copper-alumina are preferred. These catalysts may be used singly or a plurality thereof may be used.

The hydrogenation reaction in the hydrogenation step is performed by contacting α-methylstyrene and hydrogen with a hydrogenation catalyst. In an embodiment, the dehydration reaction is followed by the hydrogenation reaction, and in this aspect, a part of water generated in the dehydration reaction may be separated by performing oil-water separation or may not be separated to be contacted with a hydrogenation catalyst together with α-methylstyrene. Although the amount of hydrogen required for the hydrogenation reaction may correspond to an equimolar amount of α-methylstyrene, an excessive amount of hydrogen is used because components other than α-methylstyrene to consume hydrogen are usually contained in the raw material. Since the reaction proceeds faster as the partial pressure of hydrogen is increased, the molar ratio of hydrogen/α-methylstyrene is adjusted to usually 1/1 to 20/1, preferably 1/1 to 10/1, more preferably 1/1 to 3/1. The excessive amount of hydrogen remaining after the hydrogenation reaction may be recycled for use after separation from the reaction liquid. The hydrogenation reaction may be performed in a liquid phase in the presence of a solvent, or in a gas phase. The solvent is required to be substantially inert to the reaction raw materials and products. The solvent may be a substance present in the mixture containing α-methylstyrene. For example, in the case where the mixture containing α-methylstyrene contains cumene, the cumene can be used as the solvent and no other solvent may be used. The hydrogenation reaction temperature is usually 0 to 500° C., preferably 30 to 400° C., more preferably 50 to 300° C. The hydrogenation reaction pressure is usually 100 to 10000 kPaG, preferably 500 to 4000 kPaG, more preferably 1000 to 2000 kPaG.

The dehydration reaction and the hydrogenation reaction can be favorably performed in a slurry or a fixed bed mode. In a large-scale industrial operation, it is preferable to use a fixed bed. Further, the dehydration reaction and the hydrogenation reaction may be performed by a reaction mode such as a batch process, a semi-continuous process, and a continuous process. The dehydration reaction and the hydrogenation reaction may be performed either in separate reactors or in a single reactor. Among continuous reactors including adiabatic reactors and isothermal reactors, adiabatic reactors are preferred because isothermal reactors require equipment for heat removal.

Examples of the catalyst for use in the hydrogenolysis step (hereinafter, referred to as "hydrogenolysis catalyst") include catalysts comprising metals in group 10, group 11 or group 12 in the periodic table, specifically including catalysts comprising cobalt, catalysts comprising nickel, catalysts comprising palladium, catalysts comprising copper and catalysts comprising zinc. From the viewpoint of inhibiting formation of by-products, catalysts comprising nickel, catalysts comprising palladium or catalysts comprising copper are preferred. Examples of the catalysts comprising nickel include nickel, nickel-alumina, nickel-silica and nickel-carbon; examples of the catalysts comprising palladium include palladium-alumina, palladium-silica and palladium-carbon; and examples of the catalysts comprising copper include copper, Raney copper, copper-chromium, copper-zinc, copper-chromium-zinc, copper-silica and copper-alumina. The hydrogenolysis reaction may be performed in a liquid phase in the presence of a solvent, or in a gas phase. The solvent is required to be substantially inert to the reaction raw materials and products. The solvent may be a substance present in the residual mixture containing cumyl alcohol to be used. For example, in the case where the residual mixture containing cumyl alcohol contains cumene, the cumene can be used as the solvent and no other solvent may be used. Although the amount of hydrogen required for the hydrogenolysis reaction may correspond to an equimolar amount of cumyl alcohol, an excessive amount of hydrogen is used because components other than cumyl alcohol to consume hydrogen are usually contained in the raw material. Since the reaction proceeds faster as the partial pressure of hydrogen is increased, the molar ratio of hydrogen/cumyl alcohol is adjusted to usually 1/1 to 20/1, preferably 1/1 to 10/1, more preferably 1/1 to 3/1. The excessive amount of hydrogen remaining after the hydrogenolysis reaction may be recycled for use after separation from the reaction liquid. The hydrogenolysis reaction temperature is usually 0 to 500° C., preferably 50 to 450° C., more preferably 150 to 300° C. The hydrogenolysis reaction pressure is usually 100 to 10000 kPaG, preferably 500 to 4000 kPaG, more preferably 1000 to 2000 kPaG. The hydrogenolysis reaction can be favorably performed in a slurry or a fixed bed mode. In a large-scale industrial operation, it is preferable to use a fixed bed. Further, the hydrogenolysis reaction may be performed by a reaction mode such as a batch process, a semi-continuous process, and a continuous process.

The cumene content of the reaction mixture containing cumene is usually 90 wt % or more per 100 wt % of the reaction mixture containing cumene.

(5-2) Cumene Recovery Step

The cumene recovery step is a step of obtaining a recovery mixture containing cumene with a higher purity than before distillation by distilling the reaction mixture containing cumene obtained in the hydrogenation step. The recovery mixture containing cumene thus obtained can be recycled to the oxidation step as a raw material in the oxidation step.

The conditions for distilling the reaction mixture containing cumene obtained in the hydrogenation step are usually in the following ranges: a number of theoretical stages of 10 to 100, a pressure of −100 kPaG to 10000 kPaG, and a temperature of 0 to 500° C.; preferably, a number of theoretical stages of 10 to 95, a pressure of −100 kPaG to 5000 kPaG, and a temperature of 0 to 400° C.; and more preferably, a number of theoretical stages of 10 to 90, a pressure of −100 kPaG to 3000 kPaG; and a temperature of 0 to 300° C.

EXAMPLES

The present invention will be described below in more detail with reference to Examples as follows.

Example 1

According to the method described in the present specification, an oxidation step, a distillation step, an epoxidation step and a propylene oxide separation step were performed to produce propylene oxide.

In the oxidation step, cumene was contacted with air to obtain a reaction mixture containing cumene hydroperoxide. Subsequently, in the distillation step, the reaction mixture containing cumene hydroperoxide obtained in the oxidation step was distilled under conditions where the ratio of the flow rate of the distillate (D) to the flow rate of the reaction mixture containing cumene hydroperoxide (F), D/F, is 0.037 to be separated into a concentrate containing cumene hydroperoxide and a distillate. Note that the flow rate of the reaction mixture (F) is the weight of the reaction mixture distilled per unit time, whereas the flow rate of the distillate (D) is the weight of the distillate distilled off per unit time. The length of unit time and the unit of weight are the same between the flow rate (F) and the flow rate (D). Subsequently, in the epoxidation step, the concentrate containing cumene hydroperoxide obtained in the distillation step was contacted with propylene in the presence of a catalyst comprising a titanium-containing silicon oxide produced by a method described in Example 1 of Japanese Patent No. 3797107 in a reactor under conditions where the inlet temperature of the final reactor was 130° C., so that a reaction mixture containing propylene oxide and cumyl alcohol was obtained. The inlet temperature of the final reactor was adjusted by a heat exchanger connected upstream of the inlet of the final reactor. On this occasion, the outlet temperature of the final reactor was 130° C. Subsequently, in the separation step, the reaction mixture containing propylene oxide and cumyl alcohol obtained in the epoxidation step was distilled to separate crude propylene oxide. The methyl formate concentration of the separated crude propylene oxide was 25 ppm by weight per 100 wt % of propylene oxide based on gas chromatography analysis.

Example 2

The production of propylene oxide was performed in the same manner as in Example 1, except that in the distillation step, the reaction mixture containing cumene hydroperoxide obtained in the oxidation step was distilled under conditions where D/F was 0.062, and in the epoxidation step, the concentrate containing cumene hydroperoxide obtained in the distillation step was contacted with propylene in the reactor under conditions where the inlet temperature of the final reactor was 130° C. On this occasion, the outlet temperature of the final reactor was 131° C. In the separation step, the methyl formate concentration of the separated crude propylene oxide was 26 ppm by weight per 100 wt % of propylene oxide based on gas chromatography analysis.

Example 3

The production of propylene oxide was performed in the same manner as in Example 1, except that in the distillation step, the reaction mixture containing cumene hydroperoxide obtained in the oxidation step was distilled under conditions where D/F was 0.084, and in the epoxidation step, the concentrate containing cumene hydroperoxide obtained in the distillation step was contacted with propylene in the reactor under conditions where the inlet temperature of the final reactor was 135° C. On this occasion, the outlet temperature of the final reactor was 136° C. In the separation step, the methyl formate concentration of the separated crude propylene oxide was 27 ppm by weight per 100 wt % of propylene oxide based on gas chromatography analysis.

Example 4

The production of propylene oxide was performed in the same manner as in Example 1, except that in the distillation step, the reaction mixture containing cumene hydroperoxide obtained in the oxidation step was distilled under conditions where D/F was 0.099, and in the epoxidation step, the concentrate containing cumene hydroperoxide obtained in the distillation step was contacted with propylene in the reactor under conditions where the inlet temperature of the final reactor was 132° C. On this occasion, the outlet temperature of the final reactor was 133° C. In the separation step, the methyl formate concentration of the separated crude propylene oxide was 19 ppm by weight per 100 wt % of propylene oxide based on gas chromatography analysis.

Example 5

The production of propylene oxide was performed in the same manner as in Example 1, except that in the distillation step, the reaction mixture containing cumene hydroperoxide obtained in the oxidation step was distilled under conditions where D/F was 0.11, and in the epoxidation step, the concentrate containing cumene hydroperoxide obtained in the distillation step was contacted with propylene in the reactor under conditions where the inlet temperature of the final reactor was 104° C. On this occasion, the outlet temperature of the final reactor was 119° C. In the separation step, the methyl formate concentration of the separated crude propylene oxide was 13 ppm by weight per 100 wt % of propylene oxide based on gas chromatography analysis.

Example 6

The production of propylene oxide was performed in the same manner as in Example 1, except that in the distillation step, the reaction mixture containing cumene hydroperoxide obtained in the oxidation step was distilled under conditions where D/F was 0.13, and in the epoxidation step, the concentrate containing cumene hydroperoxide obtained in the distillation step was contacted with propylene in the reactor under conditions where the inlet temperature of the final reactor was 109° C. On this occasion, the outlet temperature of the final reactor was 120° C. In the separation step, the methyl formate concentration of the separated crude propylene oxide was 24 ppm by weight per 100 wt % of propylene oxide based on gas chromatography analysis.

Comparative Example 1

The production of propylene oxide was performed in the same manner as in Example 1, except that in the distillation step, the reaction mixture containing cumene hydroperoxide obtained in the oxidation step was distilled under conditions where D/F was 0.033, and in the epoxidation step, the concentrate containing cumene hydroperoxide obtained in the distillation step was contacted with propylene in the reactor under conditions where the inlet temperature of the final reactor was 121° C. On this occasion, the outlet temperature of the final reactor was 136° C. In the separation step, the methyl formate concentration of the separated crude propylene oxide was 147 ppm by weight per 100 wt % of propylene oxide based on gas chromatography analysis.

Comparative Example 2

The production of propylene oxide was performed in the same manner as in Example 1, except that in the distillation step, the reaction mixture containing cumene hydroperoxide obtained in the oxidation step was distilled under conditions where D/F was 0.035, and in the epoxidation step, the concentrate containing cumene hydroperoxide obtained in the distillation step was contacted with propylene in the reactor under conditions where the inlet temperature of the final reactor was 114° C. On this occasion, the outlet temperature of the final reactor was 132° C. In the separation step, the methyl formate concentration of the separated crude propylene oxide was 140 ppm by weight per 100 wt % of propylene oxide based on gas chromatography analysis.

Comparative Example 3

The production of propylene oxide was performed in the same manner as in Example 1, except that in the distillation step, the reaction mixture containing cumene hydroperoxide obtained in the oxidation step was distilled under conditions where D/F was 0.063, and in the epoxidation step, the concentrate containing cumene hydroperoxide obtained in the distillation step was contacted with propylene in the reactor under conditions where the inlet temperature of the final reactor was 129° C. On this occasion, the outlet temperature of the final reactor was 141° C. In the separation step, the methyl formate concentration of the separated crude propylene oxide was 123 ppm by weight per 100 wt % of propylene oxide based on gas chromatography analysis.

Comparative Example 4

The production of propylene oxide was performed in the same manner as in Example 1, except that in the distillation step, the reaction mixture containing cumene hydroperoxide obtained in the oxidation step was distilled under conditions where D/F was 0.073, and in the epoxidation step, the concentrate containing cumene hydroperoxide obtained in the distillation step was contacted with propylene in the reactor under conditions where the inlet temperature of the final reactor was 135° C. On this occasion, the outlet temperature of the final reactor was 142° C. In the separation step, the methyl formate concentration of the separated crude propylene oxide was 127 ppm by weight per 100 wt % of propylene oxide based on gas chromatography analysis.

As described above, provided is a method for producing propylene oxide comprising an oxidation step, a distillation step, an epoxidation step and a separation step, the method having excellent features that allows the methyl formate concentration of a reaction mixture containing propylene oxide and cumyl alcohol obtained in the epoxidation step to be controlled through control of the conditions for distilling the reaction mixture containing cumene hydroperoxide obtained in the oxidation step in the distillation step and the outlet temperature of the final reactor in the epoxidation step.

INDUSTRIAL APPLICABILITY

The present invention can be used in production of propylene oxide.

The invention claimed is:

1. A method for producing propylene oxide, the method comprising the following steps (1) to (4):
   (1) Oxidation step: a step of obtaining a reaction mixture containing cumene hydroperoxide by contacting cumene with an oxygen-containing gas to cause a reaction between cumene and oxygen in the gas;
   (2) Distillation step: a step of distilling the reaction mixture containing cumene hydroperoxide obtained in the oxidation step to be separated into a concentrate containing cumene hydroperoxide and a distillate, wherein the reaction mixture is continuously distilled under a condition where a ratio of a flow rate of the distillate (D) to a flow rate of the reaction mixture to be distilled (F), D/F, is 0.037 or more and 0.13 or less, provided that the flow rate of the reaction mixture is a weight of the reaction mixture distilled per unit time, whereas the flow rate of the distillate is a weight of the distillate distilled off per unit time;
   (3) Epoxidation step: a step of obtaining a reaction mixture containing propylene oxide, cumyl alcohol, and methyl formate by contacting the concentrate containing cumene hydroperoxide obtained in the distillation step with propylene in the presence of a catalyst comprising a titanium-containing silicon oxide in one or more reactors to cause a reaction between propylene and cumene hydroperoxide in the concentrate, wherein an outlet temperature of the final reactor of the one or more reactors is adjusted to 115° C. or more and less than 140° C.; and
   (4) Separation step: a step of separating crude propylene oxide by distilling the reaction mixture containing propylene oxide and cumyl alcohol obtained in the epoxidation step.

2. The method for producing propylene oxide according to claim 1, wherein a concentration of methyl formate in the reaction mixture is 10 ppm by weight or more and less than 30 ppm by weight based on the weight of propylene oxide in the reaction mixture.

* * * * *